(12) United States Patent
Flodin

(10) Patent No.: US 7,207,972 B2
(45) Date of Patent: Apr. 24, 2007

(54) DEVICE FOR FIXING A TUBE MEMBER

(76) Inventor: Björn Flodin, Tallåsv. 8-10, Spånga (SE) SE-163 43

( * ) Notice: Subject to any disclaimer, the term of this patent is extended or adjusted under 35 U.S.C. 154(b) by 422 days.

(21) Appl. No.: 10/381,410

(22) PCT Filed: Sep. 5, 2001

(86) PCT No.: PCT/SE01/01891

§ 371 (c)(1),
(2), (4) Date: Mar. 25, 2003

(87) PCT Pub. No.: WO02/24272

PCT Pub. Date: Mar. 28, 2002

(65) Prior Publication Data

US 2004/0138625 A1    Jul. 15, 2004

(30) Foreign Application Priority Data

Sep. 25, 2000  (SE) .................... 0003420

(51) Int. Cl.
*A61M 29/00*    (2006.01)

(52) U.S. Cl. .................... 604/103.03; 604/103.06; 604/96.01

(58) Field of Classification Search .......... 604/130.03, 604/103.05–103.09, 103.11, 533, 104–106, 604/523, 96.01, 103, 175, 910, 101.01, 101.02; 606/191–200; 128/207.14, 204.18, 200.25, 128/207.15, 200.26

See application file for complete search history.

(56) References Cited

U.S. PATENT DOCUMENTS

| | | | |
|---|---|---|---|
| 3,889,688 A | 6/1975 | Eamkaow | |
| 4,022,217 A | 5/1977 | Rowean | |
| 4,327,720 A | 5/1982 | Bronson et al. | |
| 4,351,330 A | 9/1982 | Scarberry | |
| 4,834,087 A * | 5/1989 | Coleman et al. | 128/207.14 |
| 5,397,307 A * | 3/1995 | Goodin | 604/103.07 |
| 5,470,314 A * | 11/1995 | Walinsky | 604/103.11 |
| 5,765,559 A * | 6/1998 | Kim | 128/207.15 |
| 6,117,064 A * | 9/2000 | Apple et al. | 600/3 |
| 6,391,002 B1 * | 5/2002 | Kokish | 604/96.01 |
| 6,526,977 B1 * | 3/2003 | Gobel | 128/207.14 |

FOREIGN PATENT DOCUMENTS

| GB | 2326099 A | * 6/1997 |
|---|---|---|
| GB | 2326099 | 12/1998 |

* cited by examiner

*Primary Examiner*—Nicholas Lucchesi
*Assistant Examiner*—Theodore J. Stigell
(74) *Attorney, Agent, or Firm*—Venable LLP; Eric J. Franklin

(57) ABSTRACT

A device for fixing a tube member in a cavity of a patient. The device includes a body that surrounds the tube member and has a casing that at least partly forms an inner space. The body is expandable by supplying a fluid to the inner space in such a way that the fluid in the inner space has a working pressure. Furthermore, the body has, in a non-expanded state, a relatively small outer extent, which permits the introduction into said cavity, and in an expanded state, a relatively large outer extend, which permits fixing in said cavity by abutment with a contact pressure against a tubular wall of the cavity. In order to ensure a tight abutment against the wall of the cavity, the body has such a geometrical shape that the contact pressure is substantially constant independent of variations of the working pressure within a normal working range.

10 Claims, 4 Drawing Sheets

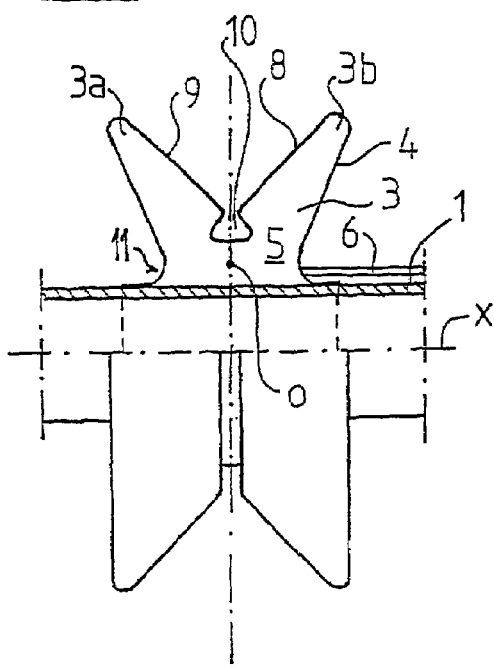
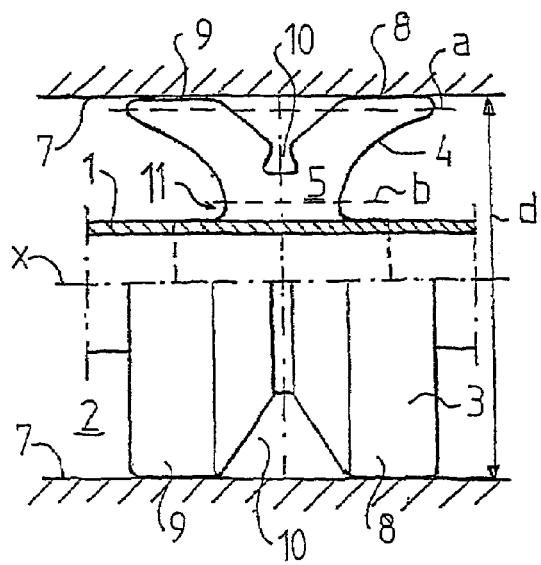
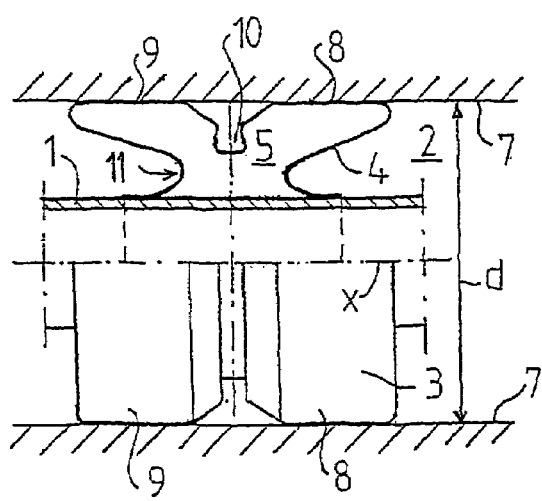
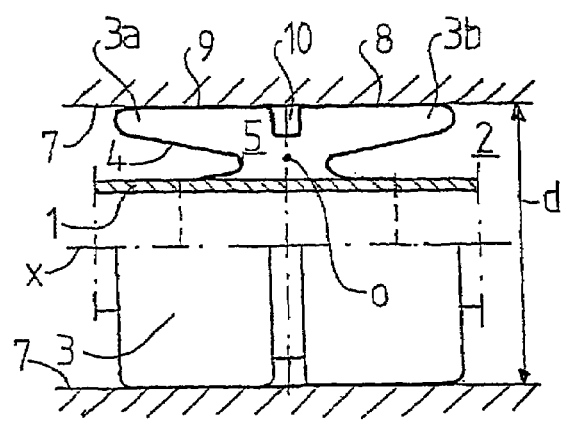

DEVICE FOR FIXING A TUBE MEMBER

CROSS-REFERENCE TO RELATED APPLICATIONS

This application claims priority to Swedish patent application 0003420-7and is the national phase under 35 U.S.C. § 371 of PCT/SE01/07891.

THE BACKGROUND OF THE INVENTION AND PRIOR ART

The present invention refers to a device for fixing a tube member in a cavity of a patient.

By such tube members, it is in the present application referred to all types of pipes, which are intended to be introduced into a patient, i.e. a human being or an animal. It may for instance be so-called endotracheal tubes, which are intended to be introduced into the trachea, corresponding tubes for the introduction into the gullet, different types of hoses, cannulae, catheters etc. for various cavities of the patient.

Frequently, it is desirable to fix such hoses or tube members in the cavities of the body of the patient in order to enable introduction and/or discharge of different fluids, i.e. liquids or gases. In that connection, the hose is to seal against an organic surface, which in its structure may be irregular as well as resilient. In order to obtain such a tight fixing, various types of fixing members are used. There are large requirements on such fixing members, in particular if the tube member also is subjected to an axial movement, bending movement, turning movement, rotation and/or if the diameter of the cavity is varying over the time, for instance by pulsation.

The organic contact surface of the cavity, against which the fixing member is to seal, consists of living material, which means that the blood supply to the surrounding tissue must not be hindered. Such an obstruction, which may appear if the contact pressure of the fixing member is too large, may rapidly result in serious consequences through the focal death of tissue.

It is known today to use inflatable balloons as fixing members, which in the inflated state are to be pressed against the wall of the cavity, and in such a way fix the tube member in the cavity and at the same time to provide a proper sealing. The inflatable balloons used today are connected with problems with regard to leakage as well as tissue injuries.

Such leakage may be very serious, for instance in connection with a respirator treatment with the use of the endotracheal tube mentioned above. If leakage arises, contaminated secretion from the upper airways may leak bypassing the balloon down to the sterile lungs and cause pneumonia. During such treatment, pressure injuries on the tissue of the mucous membrane are also frequently present when using such balloons.

The rubber/plastic materials, which have thin walls and which are used in the casings of the fixing members are permeable. Consequently, it is difficult to maintain a consistent working pressure in the balloon. Gas is diffusing outwardly, which decreases the pressure and increases the risk of leakage. The relation is opposite when using certain anaesthetic gases, which contain nitrogen oxide, wherein the gas is flowing in an opposite direction and the working pressure within the balloon increases successively with a following risk of pressure injuries on the tissue.

Such a conventional balloon, seen in a longitudinal sectional view, has a shape, which is circular, oblong or oval. It means that a changed working pressure within the balloon gives a corresponding change of the external contact pressure applied to the wall of the cavity.

Furthermore, these known balloons have in a freely inflated state a smallest given extent. If the inner extent of the cavity to be sealed by the balloon is less, small axial folds are formed on the contact surface of the balloon. Such folds lead to leakage and may also be irritating to the tissue. Also in case of a moderate turning movement of the balloon in relation to the wall of the cavity, fold formation can appear.

SUMMARY OF THE INVENTION

The object of the present invention is to remedy the problems mentioned above and to provide a fixing device, which ensures a proper sealing function and at the same time minimises the risk of pressure injuries on the tissue against which the fixing device is to abut.

This object is obtained by the device initially defined, which is characterised in that the body has, at least in the expanded state along the tube member, a relatively long extension in the proximity of the outer extent and a relatively short extension in the proximity of the tube member, wherein the body has such a geometrical shape that said contact pressure is substantially constant independent of variations of said working pressure within a normal working range.

The contact pressure will, with such a design, be provided by the geometrical or structural shape of the body rather than by the working pressure prevailing in the inner space. This is a very important improvement, since the inner working pressure will vary during use of the fixing device depending on the problems mentioned above regarding the diffusion of gas into and out of the inner space, the movement of the body in different directions in relation to the wall of the cavity, and the variation over time of the size of the cavity. The working pressure variations, which arise due to these causes, all lie within the normal working range. The present invention thus provides a fixing device, which has an improved sealing function in situations with non-shape permanent cavities and where external movements give an unfavourable influence of forces. At the same time it is possible, thanks to the substantial constant contact pressure, to reduce the risk of pressure injuries in various organic applications.

Such a body, which expands outwardly from the tube member, has a large flexibility and permits a tight continuous abutment at different radii of the cavity. Thanks to the shorter inner extension, the diameter of the outer extent of the body may vary with substantially the same contact pressure. Furthermore, the contact pressure may be kept constant if the working pressure increases or decreases since the length of the short extension may vary. The shorter extension also permits the contact surface to slope inwardly or outwardly with respect to a centre axis through the tube member, either with the same angle along the whole contact surface or with different angles for different portions. The fixing device according to the invention is thus very suitable for cavities where the wall of the cavity does not have a linear extension.

According to an embodiment of the invention, the body is, in the expanded state, arranged to form a contact surface at the outer extent, which is arranged to abut said wall. The casing may then advantageously include at least a portion, which extends inwardly into the inner space and which permits an elastic displacement of the contact surface, and more precisely outwardly, in a radial direction with regard to the centre axis in a direction towards and away from said wall, and in addition a certain axial extension. By such a portion, a substantially constant contact pressure may thus be obtained. Advantageously, said portion extends around the tube member.

According to a further embodiment of the invention, the contact surface along the tube member is longer than said short extension. By such a contact surface, which is longer than the extension of the body in the proximity of the tube member, a proper sealing against the wall of the cavity is permitted. In that connection, the contact surface may advantageously include a first surrounding surface portion and a second surrounding surface portion, wherein these surface portions are separated from each other by a surrounding depression. By such a dividing of the contact surface into two portions, the flexibility of the body is further increased. The one surface portion may then, for instance, abut the cavity wall along another extension than the extension against which the other surface portion abuts. When the device according to the invention together with the tube member is introduced into the cavity and expanded, the geometrical shape, which the body would have taken in a freely expanded state, will be deformed when the body meets the resistance of the limiting wall of the cavity. However, the body will try to take back its original shape. By the design of the reduced portions, i.e. said short extension and in certain cases also said depression, one may obtain a desired size of the flexion resistance. The flexion resistance is the contact pressure, which is transferred to the walls of the cavity, and it is, for a given design, relatively constant at different degrees of flexion. By the design according to the invention, it is rather the working pressure in the inner space, which will vary, due to external influences, without any substantial change of the contact pressure against the wall of the cavity. The reduced portions will also absorb the tendency to fold, which is present in such an expandable body, which means that the contact surface will lack all fold formations.

The geometrical shape of the body also contributes to the transfer of a direct external axial force influence on the casing to the walls of the cavity in a manner contributing to an increased security against leakage. After relief, the pressure against the wall is normalised again and such an intermittent loading and relief may in certain organic connections give a favourable "pulsation", which stimulates the blood supply to the peripheral tissue. Advantageously, the surrounding depression is designed in such a way that it does not abut said wall in the expanded state.

According to a further embodiment of the invention, the body includes two body parts. Preferably, the first surface portion is included by a first of said body parts, and the second surface portion by a second of said body parts. The two body parts are, thanks to the geometric shape, elastically flexible inwardly and outwardly, and form a respective elastically bendable lever, which is rotatable around a point in the proximity of a centre point of the body. It is also possible, to let the two body parts be separated from each other, wherein they may be provided on the tube member at a distance from each other.

According to a further embodiment of the invention, the casing is manufactured in a flexible material. The casing may then be designed in such a way that the length of said short extension in the expanded state is variable dependent on the diameter of the body with regard to the external extent and/or the relation between said working pressure and a surrounding pressure. Advantageously, the casing is also manufactured in an elastic material. The casing may have a thickness, which is substantially uniform, and be pre-shaped in such a way, that it at least partly has said geometrical shape in a rest state, i.e. in a free state when the inner pressure is substantially equal to the external surrounding pressure, and when the body is not introduced in any cavity having limiting walls.

According to a further embodiment of the invention, the casing is fixed to the tube member. The casing may then include a first end portion, which is fixed to the tube member, and a second end portion, which is fixed to the tube member, wherein the tube member between the two end portions forms a limitation of the inner space. It is also possible to design the casing in such a way that it in itself completely encloses the inner space. In this case, the body as whole may be moved onto and also displaced along a tube member for adjusting the position of the body on the tube member.

BRIEF DESCRIPTION OF THE DRAWINGS

The present invention is now to be explained more closely by a description of different embodiments and with reference to the drawings attached.

FIG. 1 discloses a partly sectional view of a device according to the invention in an expanded free state.

FIG. 2 discloses a partly sectional view of the device in FIG. 1 introduced into a cavity with a first diameter.

FIG. 3 discloses a partly sectional view of a device in FIG. 1 introduced in a cavity with a second diameter.

FIG. 4 discloses a partly sectional view of the device in FIG. 1 introduced into a cavity with a third diameter.

DETAILED DESCRIPTION OF VARIOUS EMBODIMENTS OF THE INVENTION

Figure 5:
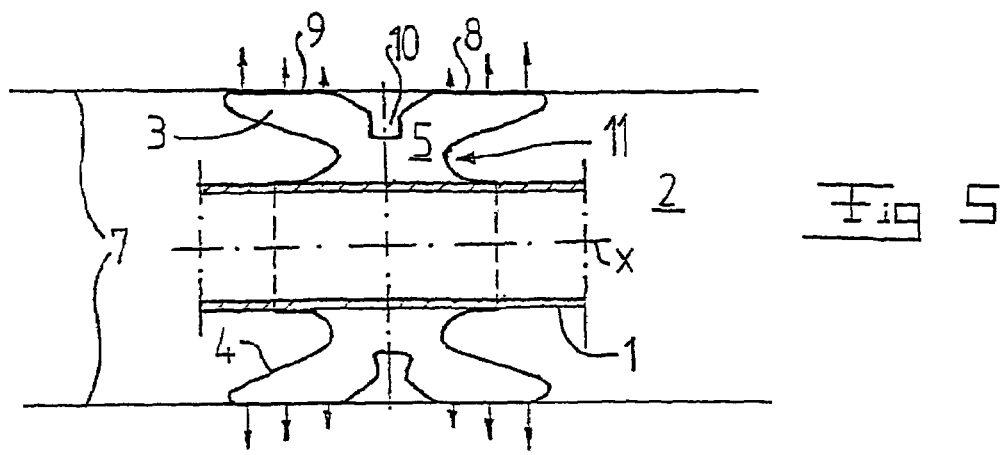
FIGS. 5–7 disclose a sectional view of the device in FIG. 1 in various states.

FIGS. 1–9 disclose an embodiment of a device for fixing a tube member 1 in a cavity 2 of a patient. FIG. 1 discloses the device in a free expanded state, i.e. the device is not introduced into any cavity 2. The device includes a body 3, which is arranged to surround the tube member 1. The body 3 is hollow and includes a casing 4, which thus at least partly encloses an inner space 5. In the embodiment disclosed, the inner space 5 is formed of the casing 4 and a portion of the outer surface of the tube member 1. It is also possible, within the scope of the invention, to let the casing 4 enclose completely the inner space 5, wherein the body 3 is provided on the tube member 1 in such a way that a part of the casing abuts the outer surface of the tube member 1. The casing 4 may according to these embodiments be fixed to the tube member 1, for instance by a permanent connection such as gluing, melting or shrinking, i.e. the casing 4 is tightened around the tube member 1. The casing 4 is flexible and manufactured in an elastic rubber-like material. Advantageously, the casing 4 has a thickness, which is substantially uniform around the inner space 5.

Figure 8:
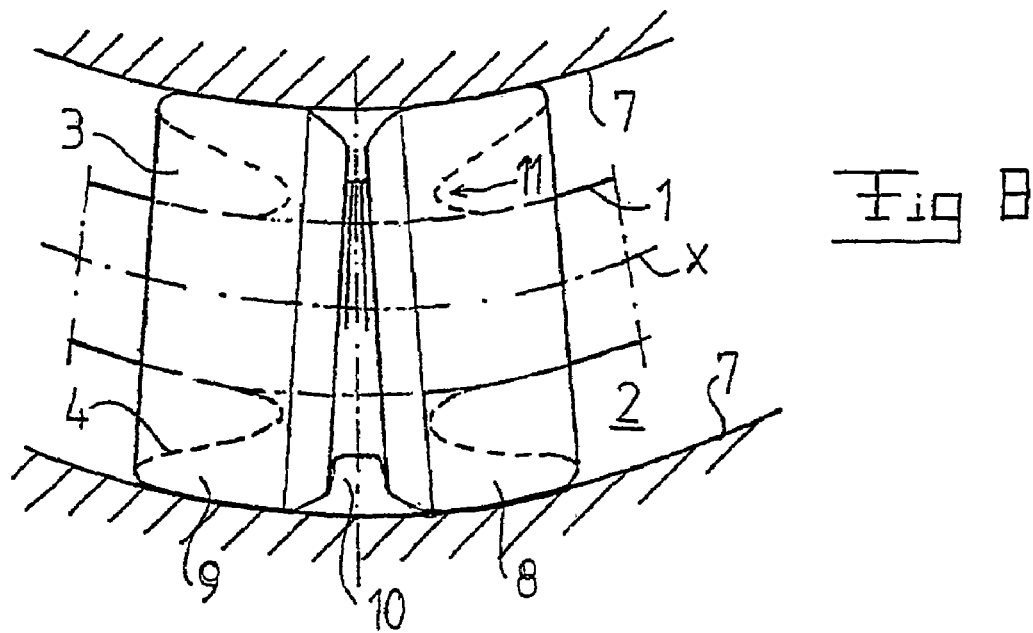
FIG. 8 discloses a view of the device introduced into a curved cavity.
Figure 9:
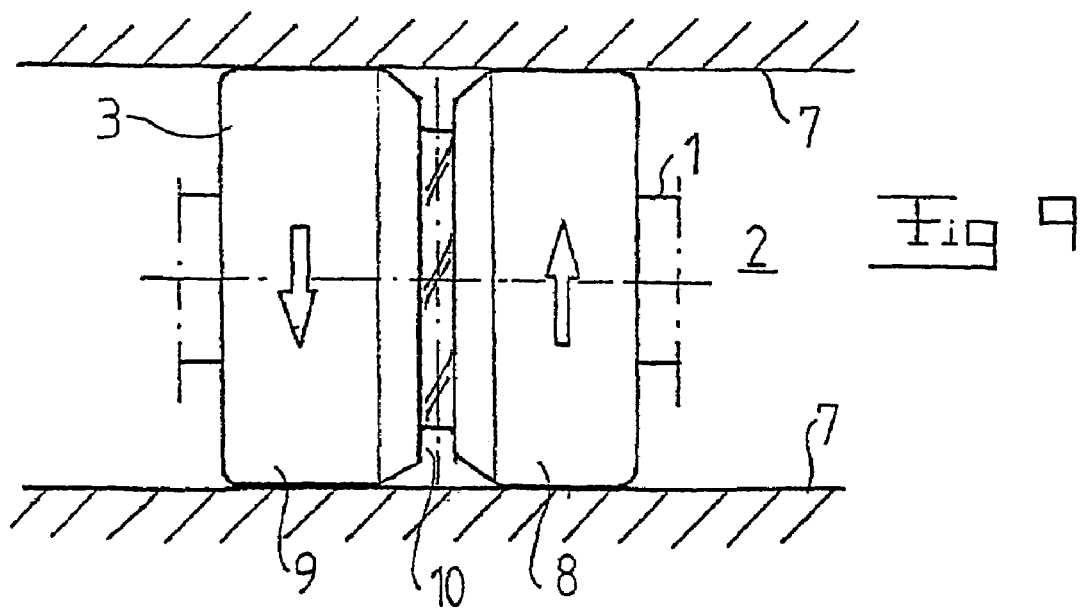
FIG. 9 discloses a view of the device in FIG. 1 subjected to turning movements.

The tube member 1 may be substantially straight as is indicated in FIGS. 1–7 and 9, or have a curved extension, as is indicated in FIG. 8. The tube member includes a centre axis x, which thus also may be straight or have a certain curvature. The centre axis x also forms a centre axis for the body 3. The device is disclosed in FIGS. 1–4, partly cut along the centre axis x and in FIGS. 5–7 completely cut along the centre axis x.

The body 3 is expandable by the supply of a fluid to the inner space 5 via supply conduit 6. The fluid may be a gas, a liquid or a foam. The supply conduit 6 is merely disclosed in Fig 1 for the sake of simplicity. The body 3 may thus be in a non-expanded state, wherein the fluid substantially has been sucked out of the inner space 5. The body may also be in an expanded state, which is disclosed in Figs 1–9, wherein the fluid has been supplied in such a way that a working pressure prevails in the inner space 5. In the non-expanded state, the body 3 has a relatively small radial, external extent, which permits the introduction into the cavity 2. In the expanded state, the body 3 has a relatively large radial, external extent, which permits fixing of the body 3 in said cavity 2 by pressing the body 3 against a tubular inner wall 7, which at least partly defines the cavity 2. The body 3 then has a contact surface, which abuts the wall 7. In the embodiment disclosed, the body 3 has two body parts 3a and 3b, wherein the contact surface includes two separate surface portions 8 and 9, one for each body part 3a and 3b, which surfaces are separated from each other by a surrounding depression or groove 10, which extends around the tube member 1 and inwardly into the inner space 5. Each body part 3a, 3b forms an elastically flexible lever, which is rotatable around a point at or in the proximity of a surrounding line 0, see Fig 4.

The body 3 has such a geometrical shape and such a structure, that the contact pressure, at which the surface portions 8 and 9 abut the wall 7, is substantially constant independent of variations of the working pressure in the inner space 5 within a normal working range, i.e. normal variations in the working pressure, which may lie between 10 and 30 mm Hg. Such normal variations of the working pressure arise due to diffusion of gas into and out of the inner space 5, movements of the body 3 in relation to the wall 7 of the cavity 2 and normal size variations of the cavity 2 over the time. The geometrical shape of the body 3 is thus structurally determined or pre-shaped in connection with the manufacture of the device. The body 3 will thus have this pre-shaped geometry in a rest state, i.e. when substantially the same pressure prevails outside the casing 4 as in the inner space 5. Also in the free state, which is disclosed in FIG. 1, the body 3 has this pre-shaped geometry.

As appears clearly from FIGS. 2–4, the body 3 has in the expanded state along the tube member 1 and the centre axis x a relatively long axial extension at or in the proximity of the outer extent, cf. the line a in FIG. 2, and a relatively short axial extension at or in the proximity of the tube member 1, cf. the line b in FIG. 2. More precisely, the contact surface, together with the depression 10 between the surface portions 8 and 9 has a longer axial extension then than the body 3 in the proximity of the tube member 1. In such a way, a portion 11 is formed, which extends around the tube member 1 and inwardly into the inner space 5 of the body 3 in the proximity of the tube member 1 when the body 3 is seen in the longitudinal section. In FIG. 2, the cavity 2 has a relatively large inner diameter d, i.e. a relatively large diameter between opposite wall surfaces of the wall 7. The shorter extension of the body 3 then has a larger length than the corresponding short extension of the body 3 when said diameter d is shorter, which appears from FIGS. 3 and 4 in comparison with FIG. 2. At the same time, the length of the body 3 increases at the radially outer extent when said diameter d decreases. At the same time, the depression 10 will decrease in its size when the above mentioned diameter d decreases. Thanks to these flexion locations, i.e. the portions 11 and 10 of the body 3, the contact pressure against the wall 7 of the cavity 2 will be substantially equal independent of the length of said diameter d.

FIG. 5 discloses schematically by means of arrows the contact force in different positions of the surface portions 8 and 9 when the body 3 is in a normal expanded state without any substantial influence from external forces.

Figure 6:
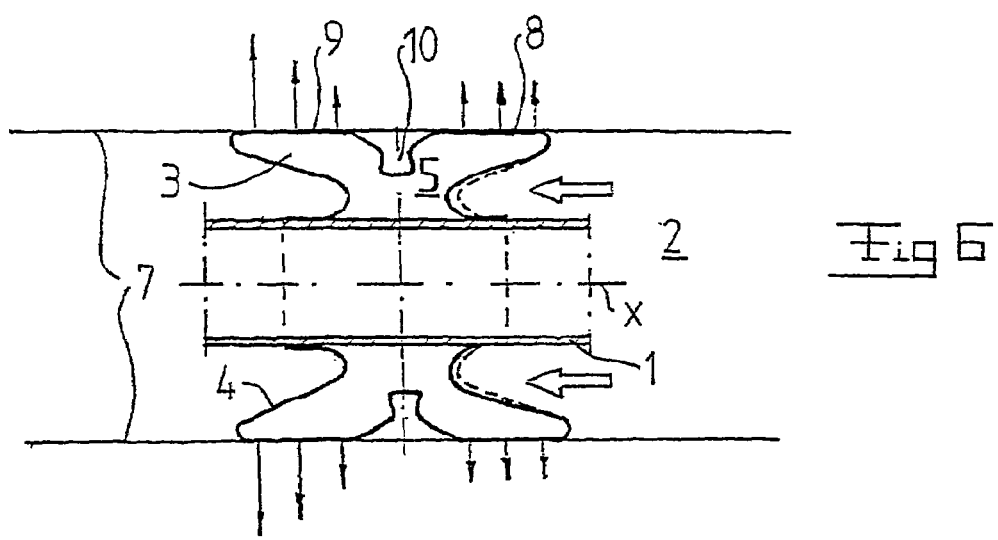
Figure 7:
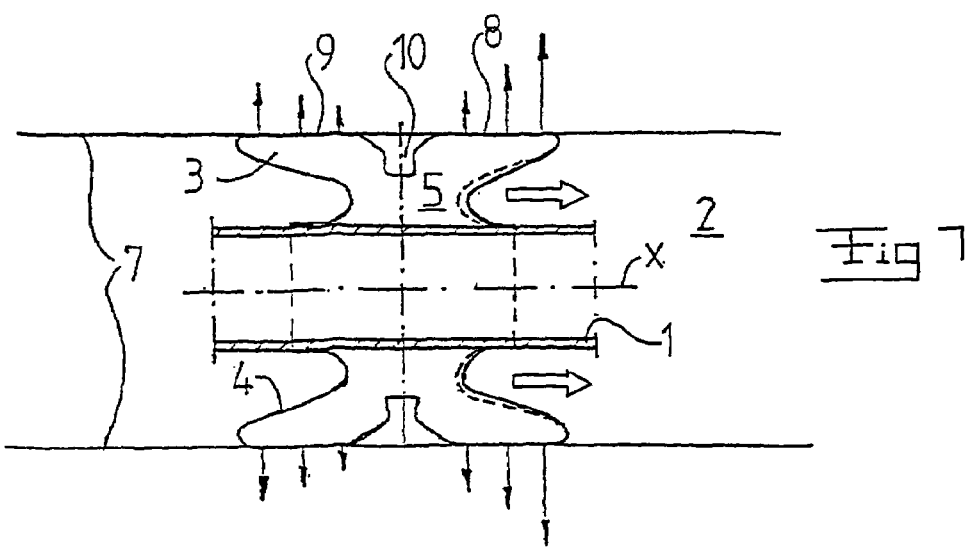

In FIG. 6, a higher pressure prevails to the right of the device than to the left thereof. This leads to the result that the waist to the right of the body 3 will be pressed inwardly, which means that the contact force against the wall 7 from the surface portion 9 increases whereas the contact force of the surface portion 8 is more uniformly distributed. In the same way, a somewhat smaller contact force is obtained from the surface portion 9 than from the surface portion 8 if the pressure is higher to the right of the device than to the left thereof, as is disclosed in FIG. 7, i.e. the waist will be displaced to the right and increase the contact force of the surface portion 8.

FIG. 8 illustrates how the two surface portions 8 and 9 maintain the tight abutment against the wall 7 with a substantially uniform contact force, even if the wall 7 is slightly curved in the direction of the axis x, at the same time as the fold formation of the surface portions 8 and 9 is prevented. The folding or the fold formation takes place in the depression 10, which is not in contact with the wall 7.

In a corresponding manner, a uniform contact pressure of the surface portions 8 and 9 may be maintained even if the two surface portions 8 are subjected to turning forces in opposite direction at the same time as fold formation of the surface portions 8 and 9 is prevented. The folding or the fold formation takes place in the depression 10, which is not in contact with the wall 7.

Figure 10:
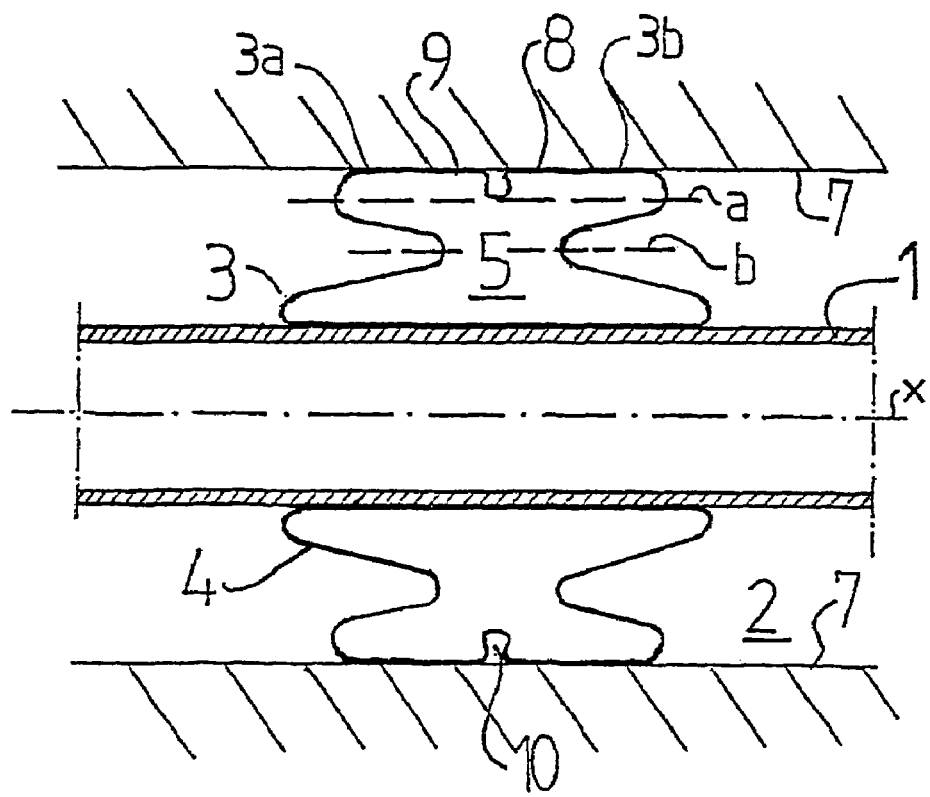
FIG. 10 discloses a sectional view of a device according to a second embodiment of the invention.

FIG. 10 discloses a second modified embodiment of the invention, according to which the body 3 has a long extension directly at the tube member 1 and a shorter extension at the line b in the proximity of the tube member 1. In the proximity of the outer extent, line a, the longitudinal extension is longer than at the line b, but shorter than directly at the tube member 1. In this embodiment, the inner space 5 is completely enclosed by the casing. The casing 4, and thus the body 3, is consequently displaceable on the tube member 1 in the direction of the centre axis x.

Figure 11:
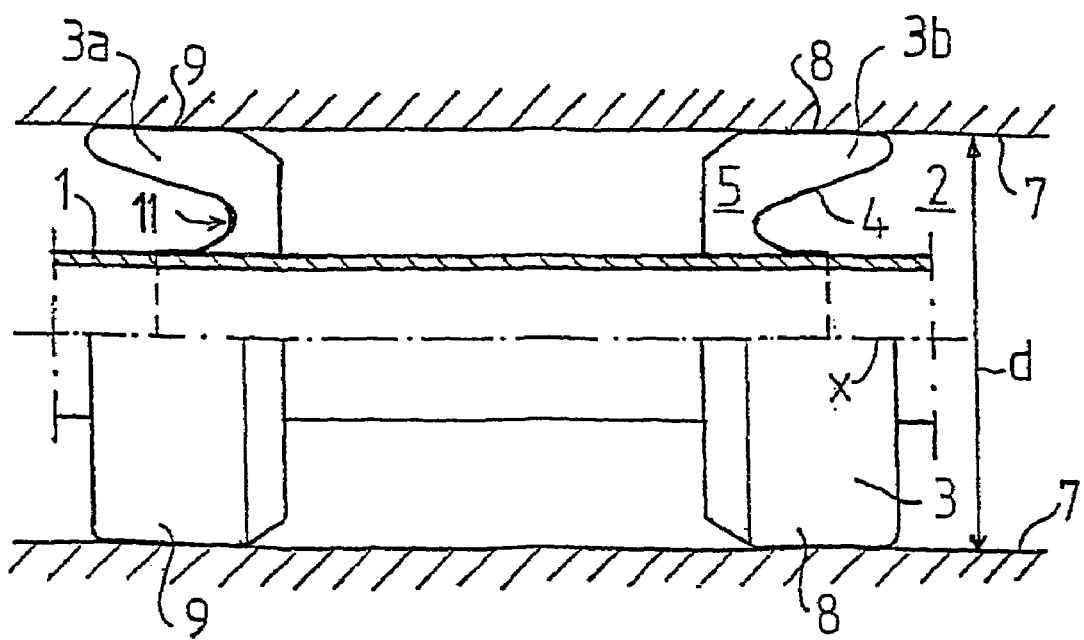
FIG. 11 discloses a sectional view of a device according to a third embodiment of the invention.

FIG. 11 discloses a third embodiment, which differs from the first and second embodiments in that the body 3 includes two separate body parts 3a and 3b, which both are attached to the tube member 1 at a distance from each other. Preferably, both body parts 3a, 3b are supplied with a fluid in such a way that substantially the same working pressure prevails in each body part 3a, 3b.

The invention is not limited to the embodiment disclosed but may be varied and modified within the scope of the following claims.

The invention claimed is:

1. An endotrachael tube, comprising:
   a tube member having a center axis; and
   a device operative to position the tube in a cavity of a patient, the device comprising an expandable body surrounding a portion of the tube member, the body comprising two body parts that at least partially enclose a single continuous inner space, each body part comprising a contact surface operative to engage a wall of the cavity in an expanded state, each contact surface extending about the center axis, the body further comprising a depression surrounding the tube member between the two body parts and extending into the inner space, wherein the body is expandable by supplying a fluid to the inner space such that the fluid in the inner space has a working pressure, wherein in an unexpanded state the body is insertable into the cavity and in the expanded state the contact surfaces abut the wall of the cavity, wherein in the expanded state the body extends a greater distance in a direction parallel to the center axis of the tube member in the vicinity of the contact surface as compared to in the vicinity of the tube member, such that the two body parts form respective elastically bendable levers, thereby resulting in the body exerting a substantially constant contact pressure on the wall of the cavity independent of variations in the working pressure of the fluid within a normal working range.

2. The endotracheal tube according to claim 1, wherein in the expanded state the body extends a greater distance in a direction parallel to the center axis of the tube member in the vicinity of the contact surface and in the vicinity of the tube member as compared to an intermediate region between the contact surface and the tube member.

3. The endotracheal tube according to claim 1, wherein the depression does not abut the wall of the cavity with the body in an expanded state.

4. The endotracheal tube according to claim 1, wherein the expandable body comprises a flexible material.

5. The endotracheal tube according to claim 1, wherein in the vicinity of the tube member the body extends a variable distance in a direction parallel to the tube member depending upon at least one of a diameter of the body, outer extent of the body, or working pressure relative to surrounding pressure.

6. The endotracheal tube according to claim 1, wherein the expandable body comprises an elastic material.

7. The endotracheal tube according to claim 1, wherein the expandable body has a substantially uniform thickness.

8. The endotracheal tube according to claim 1, wherein the expandable body is fixed to the tube member.

9. The endotracheal tube according to claim 1, wherein the expandable body comprises a first portion that is fixed to the tube member and a second portion that is fixed to the tube member, wherein between the first portion and the second portion the tube member acts as a delimitation of the inner space.

10. The endotracheal tube according to claim 1, wherein the expandable body is displaceably arranged on the tube member.

* * * * *